United States Patent
Robinson et al.

(10) Patent No.: US 6,525,091 B2
(45) Date of Patent: Feb. 25, 2003

(54) SUBSTITUTED DIARYLUREAS AS STIMULATORS FOR FAS-MEDIATED APOPTOSIS

(75) Inventors: Louise Robinson, San Carlos, CA (US); Hugo O. Villar, La Jolla, CA (US)

(73) Assignee: Telik, Inc., South San Francisco, CA (US)

( * ) Notice: Subject to any disclaimer, the term of this patent is extended or adjusted under 35 U.S.C. 154(b) by 0 days.

(21) Appl. No.: 10/082,802

(22) Filed: Feb. 22, 2002

(65) Prior Publication Data

US 2002/0188027 A1 Dec. 12, 2002

Related U.S. Application Data

(60) Provisional application No. 60/273,938, filed on Mar. 7, 2001.

(51) Int. Cl.⁷ ...................... A61K 31/17; A61K 31/255; A61K 31/275
(52) U.S. Cl. .................... 514/517; 514/518; 514/522; 514/597; 514/598; 558/24; 558/37; 558/413; 564/49; 564/50; 564/51
(58) Field of Search ................ 514/517, 518, 514/522, 597, 598; 558/24, 37, 413; 564/49, 50, 51

(56) References Cited

U.S. PATENT DOCUMENTS 4,608,205 A * 8/1986 Conrow et al. ............. 260/506

FOREIGN PATENT DOCUMENTS

| WO | 98/50346 | * 11/1998 |
| WO | 99/32463 | * 7/1999 |

* cited by examiner

*Primary Examiner*—Peter O'Sullivan
(74) *Attorney, Agent, or Firm*—Heller Ehrman White & McAuliffe LLP

(57) ABSTRACT

Substituted diarylureas, pharmaceutical compositions containing them, and their use for stimulating Fas-mediated apoptosis. The compounds, as single stereoisomers or mixtures of stereoisomers, their pharmaceutically acceptable salts, and pharmaceutical compositions containing them, are useful in methods of treating autoimmune diseases, infectious diseases, and malignancies.

20 Claims, No Drawings

SUBSTITUTED DIARYLUREAS AS STIMULATORS FOR FAS-MEDIATED APOPTOSIS

CROSS-REFERENCE TO RELATED APPLICATION

This application claims the priority under 35 USC 119(e) of U.S. Provisional Application No. 60/273,938, filed Mar. 7, 2001, which is incorporated into this application by reference.

BACKGROUND OF THE INVENTION

1. Field of the Invention

This invention relates to substituted diarylureas, to pharmaceutical compositions containing them, and to their use for stimulating Fas-mediated apoptosis.

2. Description of the Related Art

The Fas receptor, also known as APO-1 or CD95, is thought to be a key initiator of apoptotic programmed cell death in a variety of cell types. Activation of the Fas receptor by Fas ligands (FasL) or agonist antibodies leads to aggregation of the Fas receptor and recruitment of the intracellular death-inducing signal complex (DISC). See, for example, Kischkel et al., *EMBO J.* 14:5579–5588 (1995). Recruitment of other molecules, such as caspases, and in some cells, bcl-2, may also occur. It has been suggested that the main function of the Fas signaling complex is to activate caspase-8 protease. See, for example, Siegel et al., *J. Allergy Clin. Immunol.* 103:729 (1999). CD4+ T cells are unique in their ability to commit suicide by stimulating their own Fas receptors. T cells can also trigger apoptosis in B cells, macrophages, and other cell types through FasL. These interactions negatively regulate the immune system but can also contribute to immunopathology, such as in Fas-mediated damage of target tissues in hepatitis and other organ-specific autoimmune diseases. Fas plays a significant role in regulation of the human immune response, and the details of its clinical importance is being actively investigated. Altered Fas receptor or altered FasL are thought to contribute to autoimmune, infectious, and malignancies including autoimmune lymphoproliferative syndrome, autoimmune thyroid disease, hypereosinophilia, viral hepatitis, colon carcinomas, breast carcinomas, prostate cancers, neuroblastomas, gliomas, and other cancers and disease conditions. See, for example, Houghton, *J. Curr. Opin. Oncol.* 11:475 (1999) and Siegel et al., *J. Allergy Clin. Immunol.* 103:729 (1999).

There are large numbers of diarylureas cited in the literature, however there are only a limited number of diarylureas substituted with halogens. Certain diarylureas have been reported are to be useful as p38 kinase inhibitors (WO 99/32463, WO 99/00357), raf kinase inhibitors (WO 99/32436), and 5-HT receptor antagonists (WO 98/50346).

The documents cited here and elsewhere in this application are incorporated into this application by reference.

SUMMARY OF THE INVENTION

In a first aspect, this invention is compounds of the formula:

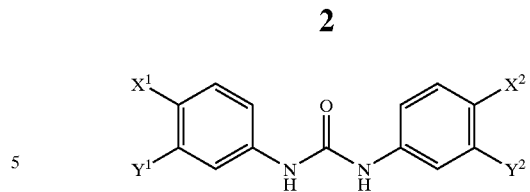

where:
$X^1$ and $X^2$ are independently selected from —F, —Cl, —Br, and —OSO$_2$R$^1$;
$Y^1$ and $Y^2$ are independently selected from —CN, —NO$_2$, —COR$^1$, —CONR$^1$R$^2$, —SO$_2$R$^1$, and —SO$_2$R$^1$R$^2$; and
each $R^1$ is independently selected from optionally substituted alkyl, optionally substituted aryl, and optionally substituted aralkyl;
each $R^2$ is independently selected from H, optionally substituted alkyl, optionally substituted aryl, and optionally substituted aralkyl,
and the pharmaceutically acceptable salts thereof.

In a second aspect, this invention is pharmaceutical compositions comprising a compound of the first aspect of the invention and a pharmaceutically acceptable excipient.

In a third aspect, this invention is methods of treating diseases in mammals treatable by administration of a stimulator of Fas-mediated apoptosis, by administering to the mammal a therapeutically effective amount of a compound of the first aspect of this invention or a composition of the second aspect of this invention. The compounds of the first aspect of this invention stimulate Fas-mediated apoptosis, leading to cell death in cells containing the Fas receptor, and are useful in the regulation of the immune system and immune responses, cell proliferation, and malignancy. Suitable diseases for such treatment are autoimmune diseases, infectious diseases, and malignancies, including autoimmune lymphoproliferative syndrome, autoimmune thyroid disease, hypereosinophilia, viral hepatitis, colon carcinomas, breast carcinomas, prostate cancers, neuroblastomas, gliomas, and other cancers and diseases. This aspect also includes the use of compounds of the first aspect of this invention in the preparation of medicaments for the treatment of diseases in mammals treatable by administration of a stimulator of Fas-mediated apoptosis.

In a fourth aspect, this invention provides a method of stimulating Fas-mediated apoptosis in a cell that has a Fas receptor, by contacting the cell with a compound of the first aspect of this invention in an amount sufficient to stimulate Fas-mediated apoptosis. In vivo, the step of contacting the cell with the compound may be effected by administering to an animal containing the cell an effective amount of the compound. In vitro, the step of contacting the cell with a compound of the formula may be effected by administering to the cell or to a solution bathing the cell an effective amount of the compound.

In a fifth aspect, this invention is methods of making the compounds of the first aspect of this invention.

DETAILED DESCRIPTION OF THE INVENTION (a) Definitions and General Parameters

"Alkyl" means a $C_1$–$C_{10}$ monovalent hydrocarbyl that may be linear, branched, or cyclic, and includes, for example, methyl, ethyl, propyl, isopropyl, butyl, isobutyl, sec-butyl, tert-butyl, pentyl, hexyl, cyclopentyl, cyclopropylmethyl, cyclohexyl, and cyclohexylmethyl. $C_{12}$–$C_6$ alkyls are preferred.

A "substituted alkyl" is an alkyl substituted with up to three halogen atoms and/or a substituent selected from —CN, —NO$_2$, —OR, —SR, —COR, —OC(O)R, —C(O)OR, —NR$_2$, —SO$_2$OR, —OSO$_2$R, —SO$_2$NR$_2$, —NRSO$_2$R, —CONR$_2$, or —NRCOR, where each R is, independently, hydrogen, optionally R'-substituted alkyl, optionally R'-substituted aryl, heteroaryl, optionally R'-substituted aralkyl, or heteroaralkyl and each R' is, independently, halo, —CN, —NO$_2$, —OH, C$_{1-3}$ alkyl, C$_{1-3}$ alkoxy, —SH, or —NH$_2$. Preferred substituted alkyls are substituted with up to three halogen atoms and/or one of the substituents selected from the group consisting of —CN, —NO$_2$, —OH, C$_{1-3}$ alkoxy, —SH, and —NH$_2$; and a particularly preferred substituted alkyl is —CF$_3$.

"Aryl" means an aromatic hydrocarbyl containing 6 to 20 ring carbon atoms, which is monocyclic (phenyl), condensed polycyclic, preferably condensed bicyclic (e.g., naphthyl), or linked polycyclic, preferably linked bicyclic (e.g., biphenylyl). The aryl is preferably C$_6$–C$_{16}$ and even more preferably, C$_6$–C$_{14}$. A particularly preferred aryl is phenyl.

A "substituted aryl" is an aryl substituted with up to three substituents selected from halo, —CN, —NO$_2$, —OR, optionally halo-substituted C$_{1-3}$ alkyl, optionally halo-substituted C$_{1-3}$ alkoxy, —SR, —COR, —OC(O)R, —C(O)OR, —NR$_2$, —SO$_2$OR, —OSO$_2$R, —SO$_2$NR$_2$, —NRSO$_2$R, —CONR$_2$, or —NRCOR, where each R is, independently, hydrogen or optionally R'-substituted alkyl and each R' is, independently, halo, —CN, —NO$_2$, —OH, C$_{1-3}$ alkyl, C$_{1-3}$ alkoxy, —SH, or —NH$_2$. Preferred substituted aryls are substituted with up to three substituents selected from the group consisting of halo, —CN, —NO$_2$, —OH, optionally halo-substituted C$_{1-3}$ alkyl, optionally halo-substituted C$_{1-3}$ alkoxy, —SH, and —NH$_2$; and particularly preferred substituted aryls are substituted phenyls.

"Aralkyl" means an alkyl substituted with an aryl. Preferred aralkyls are benzyl and phenethyl.

A "substituted aralkyl" is an aralkyl in which the aryl or the alkyl, or both, are substituted in the manner described above for substituted aryl and substituted alkyl.

"Halogen" or "halo" means F, Cl, or Br.

"Heteroaryl" means a monocyclic or condensed bicyclic aromatic hydrocarbyl containing 6 to 20 ring atoms in which 1 to 3 of the ring carbon atoms are replaced by O, S, N, or NR (where R is H or C$_{1-3}$ alkyl). Preferred heteroaryls are monocyclic containing 5 or 6 ring atoms and include furyl, thienyl, pyrrolyl, oxazolyl, imidazolyl, pyridinyl, pyrazinyl, pyridazinyl, pyrimidinyl, and the like.

"Pharmaceutically acceptable salts" are described in the section entitled "Compounds".

A "therapeutically effective amount" means that amount which, when administered to an animal for treating a disease, is sufficient to effect such treatment for the disease.

"Treating" or "treatment" of a disease in a mammal includes (1) preventing the disease from occurring in a mammal which may be predisposed to the disease but does not yet experience or display symptoms of the disease, (2) inhibiting the disease, i.e., arresting its development, (3) relieving symptoms of the disease, i.e., reducing the effects of the disease, and (4) causing regression of the disease.

(b) Compounds

In a first aspect, this invention is compounds of the formula:

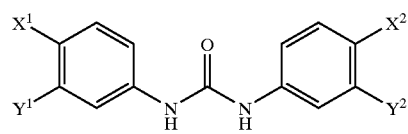

where:

X$^1$ and X$^2$ are independently selected from —F, —Cl, —Br, and —OSO$_2$R$^1$;

Y$^1$ and Y$^2$ are independently selected from —CN, —NO$_2$, —COR$^1$, —CONR$^1$R$^2$, —SO$_2$R$^1$, and —SO$_2$R$^1$R$^2$; and each R$^1$ is independently selected from optionally substituted alkyl, optionally substituted aryl, and optionally substituted aralkyl;

each R$^2$ is independently selected from H, optionally substituted alkyl, optionally substituted aryl, and optionally substituted aralkyl, and the pharmaceutically acceptable salts thereof.

Examples of preferred classes of compounds are those where one or more of the following are true:
(1) X$^1$ and X$^2$ are independently —F or —Cl,
(2) Y$^1$ and Y$^2$ are independently —CN, —NO$_2$ or —COR$^1$,
(3) X$^1$ and X$^2$ are the same, or
(4) Y$^1$ and Y$^2$ are the same.

Examples of more preferred classes of compound are those where one or more of the following are true:
(a) both X$^1$ and X$^2$ are —Cl, or both are —F, or
(b) both Y$^1$ and Y$^2$ are —NO$_2$, or both are —CN.

A particularly preferred compound is the compound where X$^1$ and X$^2$ are —Cl and Y$^1$ and Y$^2$ are —NO$_2$, i.e. the compound 1,3-bis(4-chloro-3-nitrophenyl)urea.

Syntheses and descriptions of these compounds are outlined in the Examples.

Certain compounds of the invention may contain one or more chiral centers. In such cases, all stereoisomers also fall within the scope of this invention. The invention compounds include the individually isolated stereoisomers as well as mixtures of such stereoisomers.

Pharmaceutically acceptable salts, cations and anions of the compounds of the invention are also included in the present invention and are useful in the methods and pharmaceutical compositions described herein.

Pharmaceutically acceptable salts include salts that may be formed when acidic protons present are capable of reacting with inorganic or organic bases. Typically the parent compound is treated with an excess of an alkaline reagent, such as hydroxide, carbonate or alkoxide, containing an appropriate cation. Cations such as Na$^+$, K$^+$, Ca$^{2+}$, Mg$^{2+}$ and NH$_{4+}$ are examples of cations present in pharmaceutically acceptable salts. The Na$^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If a compound of the invention contains a basic group, an acid addition salt may be prepared. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxy-ethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

Certain of the compounds may form inner salts or Zwitterions.

(c) Pharmaceutical Compositions

A second aspect of the present invention is pharmaceutical compositions comprising a compound of the first aspect of this invention and a pharmaceutically acceptable excipient.

The pharmaceutical compositions of the invention preferably comprise as an active ingredient a preferred compound of the first aspect of this invention. However, pharmaceutical compositions that comprise any of the compounds of the invention are contemplated. The pharmaceutical compositions of the invention also comprise a pharmaceutically acceptable excipient.

The compositions of this invention may be administered by any number of routes, including but not limited to, intravenous, intramuscular, intra-arterial, intramedullary, intrathecal, intraventricular, transmucosal or transdermal, subcutaneous, intraperitoneal, intranasal, enteral, sublingual, rectally or by way of other body cavity, including suppository and the like, topical, or may be administered orally. Administration may be acute, or by means of controlled-release, slow release or sustained release systems, including orally-administered time-release capsules or other delivery means, depot administration, indwelling catheter, chronic administration via a transdermal drug-delivery patch or subdermal implant, such that a relatively constant level of dosage is maintained. See, e.g., U.S. Pat. No. 3,710,795.

Formulations may be aqueous, oily, emulsified, or contain solvents suitable to the mode of administration, and may optionally be liposomal formulations, formulations designed to administer the drug across mucosal membranes or transdermal formulations. Suitable formulations for each of these and other methods of administration discussed in this application may be found, for example, in Gennaro, ed., "Remington: The Science and Practice of Pharmacy", 20th ed., 2000, Lippincott, Williams & Wilkins, Philadelphia Pa.

Depending on the intended mode of administration, pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. In addition to an effective amount of the active ingredients, the compositions may contain suitable pharmaceutically-acceptable excipients and auxiliaries which facilitate processing of the active compounds into preparations which can be used pharmaceutically. As used herein, the term "pharmaceutically acceptable excipient" refers to an excipient or mixture of excipients which does not interfere with the effectiveness of the biological activity of the active ingredients and which is not toxic to the host to which it is administered.

In addition, the pharmaceutical compositions may include other pharmaceutical agents, adjuvants, diluents, buffers, etc. The compounds may thus be administered orally, parenterally, transdermally, rectally, nasally, buccally, topically or via an implanted reservoir in dosage formulations containing conventional non-toxic pharmacologically acceptable carriers, adjuvants and vehicles. The term "parenteral" as used herein is intended to include subcutaneous, intravenous, and intramuscular injection.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The compounds of the invention may also be delivered through the skin using conventional transdermal drug delivery systems, i.e., transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art.

The pharmaceutical compositions of this invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted, or prepared in an emulsion or syrup for oral administration. Pharmaceutically acceptable solid or liquid excipients may be added to enhance or stabilize the composition, or to facilitate preparation of the composition. Liquid excipients include syrup, peanut oil, olive oil, glycerin, saline, alcohol, and water. Solid excipients include starch, lactose, calcium sulfate dihydrate, terra alba, magnesium stearate, stearic acid, talc, pectin, acacia, agar, and gelatin. The excipient may also include a sustained release material such as glyceryl monostearate or glyceryl distearate, alone or with a wax. The amount of solid excipient varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid excipient is used, the preparation will be in the form of syrup, elixir, emulsion or aqueous or non-aqueous suspension. Such a liquid formulation may be administered orally directly or filled into a soft gelatin capsule.

The pharmaceutical formulation may additionally contain one or more pharmacologically active agents in addition to a compound of the invention. These additional active agents will typically be useful for preventing or treating autoimmune, infectious and malignancies, or for enhancing the treatment of such disorders by compounds of the invention.

Some specific examples of suitable pharmaceutical compositions are described in the Examples below.

Typically, a pharmaceutical composition of the present invention is packaged in a container with a label, or instructions, or both, indicating use of the pharmaceutical composition in the treatment of autoimmune diseases, infectious diseases, malignancies, such as autoimmune lymphoproliferative syndrome, autoimmune thyroid disease, hypereosinophilia, viral hepatitis, colon carcinoma, breast carcinoma, prostate cancer, neuroblastoma, glioma, or other cancer or other disease.

(c) Methods and Uses of Compounds of this Invention.

The compounds of the invention are effective to stimulate Fas-mediated apoptosis as demonstrated in the Examples below. Stimulation of Fas-mediated apoptosis is useful, for example, in the treatment and management of subjects with autoimmune, infectious, or malignancies. More particular examples of the uses of the compounds include the treatment of autoimmune lymphoproliferative syndrome, autoimmune thyroid disease, hypereosinophilia, viral hepatitis, colon carcinomas, breast carcinomas, prostate cancers, neuroblastomas, gliomas, and other cancers and diseases.

Thus, the third aspect of this invention includes a method of treating an autoimmune disease in a mammal, preferably a human, by administering a therapeutically effective amount of a compound of the invention, or a pharmaceutical composition thereof, to the mammal. Optionally, the method may further comprise treating the mammal with a conventional form of therapy for an autoimmune disease, such as administration of a conventional immunosuppressant. Alternatively, the compounds of the invention may be administered to the mammal in combination with an anti-inflammatory agent or other conventional treatment for the symptoms of such autoimmune disease, e.g. where the disease is rheumatoid arthritis. The total amount of the combination of drugs administered to the mammal must be a therapeutically effective amount, although the amounts of each of the individual drugs may be, by themselves, suboptimal for therapeutic purposes.

The third aspect of this invention also includes a method of treating infection in a mammal, preferably a human, by administering a therapeutically effective amount of a compound of the invention, or a pharmaceutical composition thereof, to the mammal. The method may optionally further comprise treating the mammal with a conventional form of therapy for infection. For instance, an antiviral, antibacterial, or antifungal agent may also be administered to the mammal. The total amount of the combination of drugs administered to the mammal must be a therapeutically effective amount, although the individual amounts of each of the individual drugs may be, by themselves, suboptimal for therapeutic purposes.

The third aspect of this invention also includes methods of treating malignancies in a mammal, preferably a human, by administering a therapeutically effective amount of a compound of the invention, or a pharmaceutical composition thereof, to the mammal. Again, like the other treatment methods of the invention, this method may further comprise treating the mammal with a conventional form of therapy for malignancy, such as administering an anticancer chemotherapeutic agent to the mammal. The total amount of the combination of drugs administered to the mammal must be a therapeutically effective amount, although the individual amounts of each of the individual drugs may be, by themselves, suboptimal for therapeutic purposes.

The compounds of the invention, or pharmaceutical compositions thereof, are thus used to stimulate Fas-mediated apoptosis in mammals that require such treatment, by administering a therapeutically effective amount of the chosen compound, preferably dispersed in a pharmaceutical carrier. Therapeutically effective amounts of compounds of the invention are in the range of 0.01 to 1000 mg/kg, preferably 0.01 to 100 mg/kg and more preferably 1–30 mg/kg, and suitable doses will be readily determined by one skilled in the art depending upon the route of administration, age and condition of the patient. The dosage units may be administered up to one to ten times daily for acute or chronic disease. No unacceptable toxicological effects are expected when compounds of the invention are administered in accordance with the present invention.

In another aspect of the invention, Fas-mediated apoptosis is stimulated by contacting a cell having a Fas receptor with a compound of the invention in an amount sufficient to stimulate Fas-mediated apoptosis. In such a case, the contacting is effected in vivo by administering the compound, or a pharmaceutical composition thereof, to a mammal containing the cell; and in vitro by administering the compound, or a pharmaceutical composition thereof, to a container in which the cell is present or to a solution bathing the cell.

The compounds of the invention have been demonstrated to stimulate Fas-mediated apoptosis and can be useful in the treatment of autoimmune, infectious and malignancies. Similarly, other compounds which show the same effects on Fas-mediated apoptosis can be useful for the treatment of autoimmune, infectious and malignancies. The compounds disclosed in this application can be used as models to discover other new agents that act to stimulate Fas-mediated apoptosis. The steps in a process in which these compounds can be utilized to discover new therapeutic agents may be achieved by the following: the compounds may be utilized to validate, optimize, and standardize assays necessary for the discovery of other compounds that stimulate Fas-mediated apoptosis and that stimulate Fas-mediated apoptosis by action at the Fas receptor. These compounds can be utilized as benchmarks to discover other agents that show improved activity in assays that:

1. activate/stimulate the Fas receptor;
2. block the Fas receptor;
3. stimulate Fas-mediated apoptosis;
4. affect Fas-mediated regulation of cell proliferation;
5. affect Fas-mediated regulation of the immune response; and/or
6. affect Fas-mediated regulation of infection.

A method to discover agents that show improved activity in assays that activate/stimulate the Fas receptor, that block the Fas receptor, that stimulate Fas-mediated apoptosis, or that affect Fas-mediated regulation of cell proliferation, the immune response, and/or infection, comprises the steps of obtaining the results of an assay for Fas-mediated apoptosis in the presence of a plurality of concentrations of a compound of the invention, obtaining the results of the assay in the presence of a plurality of concentrations of a test compound, comparing the results of the assays, and identifying as an agent that shows improved activity in assays that measure or detect interaction with the Fas receptor, that stimulate Fas-mediated apoptosis, or that affect Fas-mediated regulation of cell proliferation, the immune response, and/or infection a test compound from which the results obtained in the assay were improved compared to the results obtained with the compound of the invention.

Algorithms may be used to compare structures or chemical properties of compounds, such as exemplary compounds and other test compounds. Algorithms may also be used to match structures or chemical properties within libraries of test compounds. In this way, where exemplary compounds or test compounds are known to have certain structures, properties, or activities of interest, compounds can be utilized to discover other compounds or agents that also have such structures, properties, or activities. For example, an activity of interest may be a desired activity in a bioassay. Such algorithms are known; for example, U.S. Pat. No. 5,567,317 and U.S. Pat. No. 5,587,293 describe methods for determining the reactivity of candidate compounds with target moieties or receptors. A formula predictive of reactivity with the target receptor may be obtained from a reference set of receptors or from a panel of compounds that are systematically diverse with respect to certain properties. Compounds to be tested in this way can be physically assessed with respect to the reference receptors, the formula applied, and the expected reactivity with the actual target receptor may be predicted. The method of U.S. Pat. No. 5,587,293 does not require the physical presence of the receptor.

The use of such algorithms that compare structures or chemical properties and/or match structures or chemical properties within libraries of test compounds, is effective to discover agents that display activity in bioassays. Such bioassays include bioassays to detect and measure interaction with the Fas receptor, blockade of the Fas receptor, Fas-mediated apoptosis, activation of Fas-mediated apoptosis, stimulation of Fas-mediated apoptosis, and effects on Fas-mediated regulation of cell proliferation, Fas-mediated regulation of the immune response, and Fas-mediated regulation of infection.

In addition, when combined with algorithms that compare structures or chemical properties and/or match structures or chemical properties within libraries of test compounds, these compounds can be utilized to discover agents that display activity in bioassays that:

1. activate/stimulate the Fas receptor;
2. block the Fas receptor;
3. stimulate Fas-mediated apoptosis;
4. affect Fas-mediated regulation of cell proliferation;

5. affect Fas-mediated regulation of the immune response; and/or
6. affect Fas-mediated regulation of infection.

A method to discover agents that display activity in bioassays that activate/stimulate the Fas receptor, that block the Fas receptor, that stimulate Fas-mediated apoptosis, or that affect Fas-mediated regulation of cell proliferation, the immune response, and/or infection, comprising applying an algorithm to compare the chemical structures or chemical properties within a library of test compounds with the chemical structure or chemical properties of a compound of the invention, and identifying as an agent that displays activity in bioassays that activate/stimulate the Fas receptor, that block the Fas receptor, that stimulate Fas-mediated apoptosis, or that affect Fas-mediated regulation of cell proliferation, the immune response, and/or infection, a test compound determined by the algorithm to have a chemical structure or chemical properties similar to the compound of the invention.

Algorithms may also be used to compare structures and/or match structures for the purpose of modeling molecular interactions. Such algorithms are known; for example, the methods of U.S. Pat. No. 5,567,317 and U.S. Pat. No. 5,587,293 may be used to compare structures and/or match structures for the purpose of modeling molecular interactions.

The use of such algorithms is effective to discover agents that display activity in bioassays such as bioassays to detect and measure interaction with the Fas receptor, blockade of the Fas receptor, Fas-mediated apoptosis, activation of Fas-mediated apoptosis, stimulation of Fas-mediated apoptosis, and effects on Fas-mediated regulation of cell proliferation, Fas-mediated regulation of the immune response, and Fas-mediated regulation of infection.

Further, when combined with algorithms that compare structures and/or match structures for the purpose of modeling molecular interactions, these compounds can be utilized to discover agents that display activity in bioassays that:
1. activate/stimulate the Fas receptor;
2. block the Fas receptor;
3. stimulate Fas-mediated apoptosis;
4. affect Fas-mediated regulation of cell proliferation;
5. affect Fas-mediated regulation of the immune response; and/or
6. affect Fas-mediated regulation of infection.

A method to discover agents that display activity in bioassays that activate/stimulate the Fas receptor, that block the Fas receptor, that stimulate Fas-mediated apoptosis, or that affect Fas-mediated regulation of cell proliferation, the immune response, and/or infection, comprising applying an algorithm to compare and/or match the chemical structures within a library of test compounds with the chemical structure of a compound of the invention for the purpose of modeling molecular interactions, and identifying as an agent that activates/stimulates the Fas receptor, that blocks the Fas receptor, that stimulates Fas-mediated apoptosis, or that affects Fas-mediated regulation of cell proliferation, the immune response, and/or infection, a test compound determined by the algorithm to have chemical structure comparable to or matching the compound of the invention.

In addition, the methods of the invention include a process for validating, optimizing, or standardizing a bioassay. This process comprises (a) submitting a compound of the invention to the bioassay; and (b), validating, optimizing, or standardizing the bioassay by the activity of the compound in the bioassay.

EXAMPLES

The following Examples illustrate this invention, and are in no way intended to limit the scope of this invention.

The compounds of this invention are prepared by conventional methods of organic chemistry, and many methods for the synthesis of substituted ureas are well known to the art. See, for example, Larock, "Comprehensive Organic Transformations", Wiley-VCH, New York N.Y. In some cases, protective groups may be introduced and later removed. Suitable protective groups for amino, hydroxyl, and carboxyl groups are described in Greene et al. "Protective Groups in Organic Synthesis", 2nd ed., 1991, John Wiley and Sons, New York N.Y. The compounds of this invention can be synthesized as shown in the following examples or by modifying the exemplified syntheses by means known to those of ordinary skill in the art.

A typical synthesis that is convenient for both symmetrical and unsymmetrical diarylureas is shown in Reaction Scheme 1 below. The reaction of an isocyanate 2 (conveniently prepared by reaction of a first amine 1 and phosgene in a basic solution) with a second amine 3 in a basic solution affords urea 4. In this scheme, each of $X^1$ and $X^2$ may be the same, or may be different, and similarly each of $Y^1$ and $Y^2$ may be the same, or may be different.

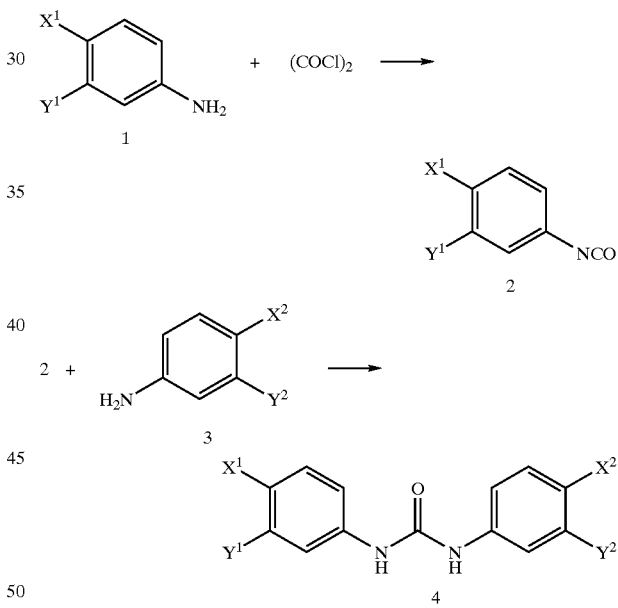

Reaction Scheme 1

Example 1

1-(4-chloro-3-cyanophenyl)-3-(4-chloro-3-nitrophenyl)urea

A solution of 3-nitro-4-chloroaniline (2 g) in 50 mL benzene and 5 mL triethylamine was added dropwise to a stirred solution of 20% w/w phosgene in toluene (6 g) and 10 mL benzene at 5° C. Once addition was completed, the reaction mixture was warmed to room temperature and stirring was continued for 3 hours to form the isocyanate; then 2.1 g 3-cyano-4-chloroaniline in 10 mL of benzene was added dropwise to the isocyanate solution. The reaction mixture was stirred at 65° C. overnight. The solution was cooled to room temperature, and 100 mL diethyl ether was added to precipitate the product and amine salts. The slurry was filtered using a fritted funnel and washed with diethyl ether. The solids were re-slurried with water and washed with water, 10% hydrochloric acid (twice), and distilled water (three times). The product was air dried to give 2.9 grams (72%) of 1-(4-chloro-3-cyanophenyl)-3-(4-chloro-3-nitrophenyl)urea.

As shown in Reaction Scheme 2, symmetrical ureas can be conveniently prepared by treating an isocyanate 5 (which may, of course, have been prepared from an amine as described above) with water to hydrolyze some of the isocyanate back to the amine, whereupon the subsequent condensation of the amine with the remaining isocyanate yields the appropriate symmetrical urea 6.

Reaction Scheme 2

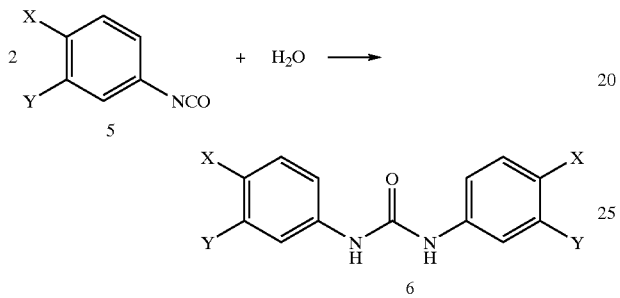

Example 2

1,3-bis(4-chloro-3-nitrophenyl)urea

A solution of 3-nitro-4-chloroaniline (2 g) in 50 mL benzene, 5 mL pyridine, and 100 mg 4-dimethylaminopyridine was added dropwise to a stirred solution of 20% w/w phosgene in toluene (6 g) and 10 mL benzene at 5° C. Once the addition was completed, the reaction mixture was warmed to room temperature and stirring was continued for 3 hours. This solution was then added to a stirred mixture of 200 mL diethyl ether, 0.5 mL pyridine, and 100 mg water, and stirred overnight. An additional 10 mL of water was added, and stirring was continued for 1 hour. The resulting precipitate was filtered using a fritted funnel and washed with diethyl ether. The solids were re-slurried with water and washed with water, 10% hydrochloric acid (twice), and distilled water (until the wash water was neutral pH). The product was air dried to give 0.97 g (47%) of 1,3-bis(4-chloro-3-nitrophenyl)urea.

The table gives representative examples of compounds of this invention.

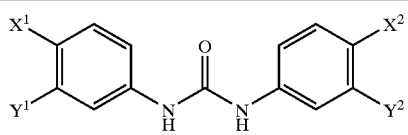

| Compound No. | $X^1$ | $X^2$ | $Y^1$ | $Y^2$ |
|---|---|---|---|---|
| 1 | Cl | Cl | $NO_2$ | $NO_2$ |
| 2 | F | F | $NO_2$ | $NO_2$ |
| 3 | Br | Br | $NO_2$ | $NO_2$ |
| 4 | Cl | Cl | CN | CN |
| 5 | F | F | CN | CN |

-continued

| Compound No. | $X^1$ | $X^2$ | $Y^1$ | $Y^2$ |
|---|---|---|---|---|
| 6 | Br | Br | CN | CN |
| 7 | Cl | Cl | $SO_2CF_3$ | $SO_2CF_3$ |
| 8 | F | F | $SO_2CF_3$ | $SO_2CF_3$ |
| 9 | Br | Br | $SO_2CF_3$ | $SO_2CF_3$ |
| 10 | Cl | Cl | $SO_2CH_3$ | $SO_2CH_3$ |
| 11 | F | F | $SO_2CH_3$ | $SO_2CH_3$ |
| 12 | Cl | Cl | $SO_2Ph$ | $SO_2Ph$ |
| 13 | F | F | $SO_2Ph$ | $SO_2Ph$ |
| 14 | F | Cl | CN | CN |
| 15 | F | Cl | $NO_2$ | $NO_2$ |
| 16 | Br | Cl | $NO_2$ | $NO_2$ |
| 17 | F | Cl | $SO_2CH_3$ | $SO_2CH_3$ |
| 18 | F | F | $COCH_3$ | $COCH_3$ |
| 19 | Cl | Cl | $COCH_3$ | $COCH_3$ |
| 20 | F | F | $CONHCH_3$ | $CONHCH_3$ |
| 21 | Cl | F | $CON(CH_3)_2$ | $CON(CH_3)_2$ |
| 22 | Cl | Cl | $CON(CH_3)_2$ | $COCH_3$ |
| 23 | Br | Cl | $NO_2$ | CN |
| 24 | F | F | $NO_2$ | CN |
| 25 | F | Cl | $NO_2$ | CN |
| 26 | Cl | F | $NO_2$ | CN |
| 27 | Cl | Cl | $COCH_3$ | CN |
| 28 | Cl | Cl | $COCH_3$ | $NO_2$ |
| 29 | F | Cl | $COCH_3$ | $NO_2$ |
| 30 | Cl | Cl | $SO_2CF_3$ | $NO_2$ |
| 31 | Cl | F | $SO_2CF_3$ | $SO_2CH_3$ |
| 32 | Cl | F | $SO_2CF_3$ | $NO_2$ |
| 33 | Cl | F | $SO_2CF_3$ | CN |
| 34 | F | F | $SO_2CH_3$ | $NO_2$ |
| 35 | Cl | Cl | $SO_2CH_3$ | $NO_2$ |
| 36 | F | Cl | $SO_2CH_3$ | $NO_2$ |
| 37 | Cl | Cl | COPh | $NO_2$ |
| 38 | F | Cl | $SO_2Ph$ | $NO_2$ |
| 39 | F | F | $SO_2Ph$ | $NO_2$ |
| 40 | Cl | Cl | $SO_2Ph$ | $NO_2$ |
| 41 | F | Cl | $SO_2Ph$ | CN |
| 42 | F | F | $SO_2Ph$ | $NO_2$ |
| 43 | F | Cl | $SO_2Ph$ | $SO_2Ph$ |
| 44 | Cl | F | $CON(CH_3)_2$ | $NO_2$ |
| 45 | F | F | $CON(CH_3)_2$ | $NO_2$ |
| 46 | Cl | Cl | $CON(CH_3)_2$ | $NO_2$ |
| 47 | Cl | Br | $CON(CH_3)_2$ | $NO_2$ |
| 48 | $OSO_2CF_3$ | $OSO_2CF_3$ | $NO_2$ | $NO_2$ |
| 49 | $OSO_2CH_3$ | Cl | $NO_2$ | $NO_2$ |
| 50 | $OSO_2CF_3$ | F | $NO_2$ | $NO_2$ |

Example 3

Fas-mediated Apoptosis

Assays for Fas-dependent apoptosis are known in the art. See, for example, Ruiz-Ruiz et al, *Cell Death Diff.* 271 (1999); and Muller et al., *J. Exp. Therap.* 188:2033 (1998).

Apoptosis is identified by detection of the DNA fragmentation pattern characteristic of apoptotic cell death. In this Example, apoptosis is detected and measured by FACS® analysis carried out in a FACScan® flow cytometer (Becton Dickinson) using CellQuest software. Quantification of DNA fragmentation is performed by FACS® analysis of propidium iodide-stained nuclei as described in Nicolletti et al., *J. Immunol. Methods* 139:271–279 (1991). Hepatocytes floating in the culture medium are collected by centrifugation at 200×g. Adherent hepatocytes are harvested by incubation with 1% trypsin for 1 min. The cells are washed in phosphate-buffered saline (PBS), suspended in hypotonic lysis buffer (0.1% sodium citrate, 0.1% Triton X, and 50 ng/mL propidium iodide) (Sigma) and incubated at 4° C. for 6 hours. Cells are then analyzed for DNA content by flow cytometry.

Early apoptotic changes are identified using annexin V-Fluos (Boehringer Mannheim) which binds to phosphatidylserine molecules (PS) exposed on apoptotic, but not normal, cell membranes (PS is normally restricted to the inner leaflet of the cell membrane bilayer). Propidium iodide is used to discriminate necrotic cells from the annexin V positively stained cell cluster. Cells are typsinized, washed with PBS, centrifuged at 200×g for 5 min, and resuspended in 100 µL HEPES buffer (10 ml HEPES/NaOH, pH 7.4, 140 mM NaCl, 5 mM $CaCl_2$) and 20 µL propidium iodide. Cells are incubated for 10–15 min and analyzed on a flow cytometer using CellQuest software. A 488 nm excitation wavelength and a 560 nm cutoff filter is used for detection of propidium iodide.

Compound 3 shows stimulation of Fas-dependent apoptosis at 10 µM.

Example 4

Stimulation of Fas-mediated Apoptosis

Anti-human Fas antibody h-HFE7A, humanized antibody was obtained from Sankyo Co., Ltd. This antibody induces apoptosis when cross-linked with secondary antibody in vitro.

Samples of human synovium were obtained from rheumatoid arthritis patients at the time of total knee replacement surgery or synoviectomy. Synovial tissue was minced into small pieces and was digested with collagenase and cultured in Ham's F12 medium supplemented with 10% fetal bovine serum (F10F) in a humidified 5% $CO_2$ atmosphere at 37° C. Adherent cells were considered as synoviocytes and were cultivated in F10 F.

Cell viability was determined with the XTT method described in *Cancer Res.* 48:4827 (1988). Ninety-six well flat plates were precoated with anti-human IgG. h-HFE7A (1000 ng/mL) and/or 10 µM of a compound of this invention were added and incubated for 2 hours. Synoviocytes were seeded (10,000/well) and incubated for 16 hours. Background wells received culture medium only. XTT (2,3-Bis [2-methoxy-4-nitro-sulfophenyl]-2H-tetrazolium-5-carboxanilide), final concentration 200 µg/mL, and phenazine methosulfate, final concentration 5 µM, were added to each well, and further incubated for 4 hours. The absorbance at 450 nm was measured and cell viability was determined as follows:

$$\text{Cell viability}(\%) = \frac{(OD_{450} \text{ of test sample} - OD_{450} \text{ of background}) \times 100}{(OD_{450} \text{ of control sample} - OD_{450} \text{ of background})}$$

Enhancement of Fas-mediated apoptosis by compounds of this invention was determined by the stimulation index (SI):

$$SI = \frac{((\text{Cell viability}(\%) \text{ with compound only}) \times (\text{Cell viability}(\%) \text{ with h-HFE7A only}))}{(\text{Cell viability}(\%) \text{ with compound and h-HEF7A}) \times 100}$$

An SI over 2.0 was considered positive.

Compound 3 was positive in this assay at 10 µM.

Example 5

Expression of the Fas Receptor

Expression of the Fas receptor is measured by the method of Muller et al., *J Exp. Med.* 188:2033–2045 (1998). A FACScan® flow cytometer (Becton Dickinson) using CellQuest software is used to determine the percent enhanced Fas receptor expression. The antibody anti-APO-1 (IgG3), specific for the Fas receptor, is used as a purified biotinylated antibody. Quantum Red streptavidin (Sigma) is used as a secondary reagent for indirect immunofluorescence. Hepatoma cells are incubated in 50 µL culture medium with biotinylated anti-APO-1. After 30 min incubation, cells are washed twice, incubated for 30 min with Quantum Red streptavidin, washed twice again, and assayed. Upon data acquisition, a gate is set on intact cells by forward/side scatter analysis, and $10^4$ viable cells are analyzed. The percent enhanced Fas receptor expression is calculated as the difference between the % Fas receptor detected in treated cells and the % Fas receptor detected in control cells, according to the formula:

Enhanced Fas receptor expression (%)=(% Fas receptor in treated cells–% Quantum Red in treated cells)–(% Fas receptor in control cells–% Quantum Red in control cells).

Compounds of the invention are found to enhance Fas receptor expression.

Example 6

Oral Pharmaceutical Composition Preparation—Solid Dosage Formulation

A pharmaceutical composition for oral administration is prepared by combining the following:

|  | % w/w |
|---|---|
| Compound of the invention | 10% |
| Magnesium stearate | 0.5% |
| Starch | 2.0% |
| hydroxypropylmethylcellulose | 1.0% |
| Microcrystalline cellulose | 86.5% |

The mixture is compressed in a press to form tablets. Alternatively, the mixture is instead filled into hard gelatin capsules.

Tablets may be coated by applying a suspension of film former (e.g. hydroxypropyl-methylcellulose), pigment (e.g. titanium dioxide) and plasticizer (e.g. diethyl phthalate) and drying the film by evaporation of the solvent. The film coat is typically between 2% and 6% of the tablet by weight, e.g. 3% by weight.

Tablets comprising compounds of the invention made by the methods of this Example are suitable for oral administration and are effective in the enhancement of Fas-mediated apoptosis and for the treatment of autoimmune diseases, infectious diseases, and malignancies.

Example 7

Oral Pharmaceutical Composition Preparation—Softgel

A pharmaceutical composition of a compound of the invention suitable for oral administration is prepared by combining the following:

| | % w/w |
|---|---|
| Compound of the invention | 20% |
| Polyethylene glycol | 80% |

The compound is dispersed or dissolved in the liquid carrier, and a thickening agent is optionally added. The formulation is then enclosed in a soft gelatin capsule.

Soft gelatin capsules comprising compounds of the invention made by the methods of this example are suitable for oral administration and are effective in the enhancement of Fas-mediated apoptosis and for the treatment of autoimmune diseases, infectious diseases, and malignancies.

Example 8

Pharmaceutical Composition for Parenteral Administration

Pharmaceutical compositions for parenteral administration typically comprise the pharmaceutically active ingredient and physiological saline, such as phosphate buffered saline or other water solution with pH and salt content suitable for introduction into an animal. A pharmaceutical composition for parenteral administration is prepared by combining a compound of the invention and Dulbecco's Phosphate Buffered Saline (D8662, Sigma Chemical Co. St. Louis Mo.) as described in the following:

| | % w/w |
|---|---|
| Compound of the invention | 1.0% |
| Saline | 99.0% |

The solution is sterilized and sealed in sterile containers.

Pharmaceutical compositions comprising compounds of the invention made by the methods of this example are suitable for parenteral administration and are effective in the enhancement of Fas-mediated apoptosis and for the treatment of autoimmune diseases, infectious diseases, and malignancies.

Various modifications and variations of the present invention will be apparent to those skilled in the art without departing from the scope and spirit of the invention. Although the invention has been described in connection with specific preferred embodiments, it should be understood that the invention as claimed is not limited to such specific embodiments. It will be appreciated by one of ordinary skill in the art that various modifications of the described modes for carrying out the invention are within the scope of the following claims.

We claim:

1. A compound of the formula:

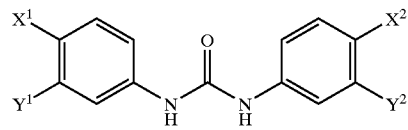

where:

$X^1$ and $X^2$ are independently selected from —F, —Cl, —Br, and —$OSO_2R^1$;

$Y^1$ and $Y^2$ are independently selected from —CN, —$NO_2$, —$COR^1$, —$CONR^1R^2$, —$SO_2R^1$, and —$SO_2R^1R^2$; and each $R^1$ is independently selected from optionally substituted alkyl, optionally substituted aryl, and optionally substituted aralkyl;

each $R^2$ is independently selected from H, optionally substituted alkyl, optionally substituted aryl, and optionally substituted aralkyl, or a pharmaceutically acceptable salt thereof.

2. A compound of claim 1, where $X^1$ and $X^2$ are the same.

3. A compound of claim 1, where $Y^1$ and $Y^2$ are the same.

4. A compound of claim 1, where $X^1$ and $X^2$ are independently selected from —F and —Cl.

5. A compound of claim 1, where $Y^1$ and $Y^2$ are independently selected from —CN, —$NO_2$, and —$COR^1$.

6. The compound of claim 1 which is 1,3-bis(4-chloro-3-nitrophenyl)urea.

7. A pharmaceutical composition comprising:
a compound of claim 1, and
a pharmaceutically acceptable excipient.

8. A pharmaceutical composition comprising:
a compound of claim 2, and
a pharmaceutically acceptable excipient.

9. A pharmaceutical composition comprising:
a compound of claim 3, and
a pharmaceutically acceptable excipient.

10. A pharmaceutical composition comprising:
a compound of claim 4, and
a pharmaceutically acceptable excipient.

11. A pharmaceutical composition comprising:
a compound of claim 5, and
a pharmaceutically acceptable excipient.

12. A pharmaceutical composition comprising:
a compound of claim 6, and
a pharmaceutically acceptable excipient.

13. A method of treating a disease in a mammal treatable by administration of a stimulator of Fas-mediated apoptosis, comprising:
administering to the mammal a therapeutically effective amount of a compound of claim 1.

14. The method of claim 13, where the disease is selected from the group consisting of autoimmune diseases, infectious diseases, and malignancies.

15. The method of claim 14, further comprising treating said mammal with a conventional form of therapy for the disease.

16. The method of claim 15, where the conventional form-of therapy comprises administering a drug selected from the group consisting of immunosuppressants, antiinflammatory agents, antiviral agents, antibacterial agents, antifungal agents, and anticancer chemotherapeutic agents.

17. A method of stimulating Fas-mediated apoptosis in a cell with a Fas receptor, comprising contacting the cell with a compound of claim 1 in an amount sufficient to stimulate the Fas receptor.

18. A process for identifying a compound that has at least one function selected from the group of stimulating the Fas receptor and stimulating Fas-mediated apoptosis, the process comprising administering to an assay of Fas binding or of Fas-mediated apoptosis a compound of claim 1 and noting a first result, administering a test compound to the assay and noting a second result, and comparing the first and second results, whereby a test compound producing results similar to or better than the first result is identified as a compound having the desired function.

19. A process for identifying a target compound that mimics the function of a compound of claim 1 in an assay, the process comprising administering a compound of claim 1 to the assay and noting a first result, administering a test compound to the assay and noting a second result, and comparing the first and second results, whereby a test compound producing results similar to or better than the first result is identified as a target compound that mimics the function of a compound of claim 1.

20. A process for validating, optimizing, or standardizing a bioassay, the process comprising submitting a compound of claim 1 to the bioassay; and validating, optimizing, or standardizing the bioassay by the activity of the compound in the bioassay.

* * * * *

UNITED STATES PATENT AND TRADEMARK OFFICE
CERTIFICATE OF CORRECTION

PATENT NO.    : 6,525,091 B2
DATED         : February 25, 2003
INVENTOR(S)   : Louise Robinson and Hugo O. Villar It is certified that error appears in the above-identified patent and that said Letters Patent is hereby corrected as shown below:

Column 2,
Line 13, "—$SO_2R^1R^2$" should be -- —$SO_2NR^1R^2$ --.

Column 4,
Line 12, "—$SO_2R^1R^2$" should be -- —$SO_2NR^1R^2$ --.

Column 18,
Line 16, "—$SO_2R^1R^2$" should be -- —$SO_2NR^1R^2$ --.

Signed and Sealed this

Eighth Day of July, 2003

JAMES E. ROGAN
*Director of the United States Patent and Trademark Office*